(12) United States Patent
Roseman

(10) Patent No.: US 11,241,342 B2
(45) Date of Patent: Feb. 8, 2022

(54) DISPOSABLE MENSTRUAL UNDERGARMENT

(71) Applicant: Tiffany Roseman, Miami, FL (US)

(72) Inventor: Tiffany Roseman, Miami, FL (US)

(73) Assignee: Tiffany Roseman, Miami, FL (US)

( * ) Notice: Subject to any disclaimer, the term of this patent is extended or adjusted under 35 U.S.C. 154(b) by 0 days.

(21) Appl. No.: 14/534,448

(22) Filed: Nov. 6, 2014

(65) Prior Publication Data

US 2016/0128879 A1    May 12, 2016

(51) Int. Cl.
*A61F 13/15*    (2006.01)
*A61F 13/74*    (2006.01)

(52) U.S. Cl.
CPC .................................... *A61F 13/74* (2013.01)

(58) Field of Classification Search
CPC ......... A61F 13/665; A61F 13/74; A61F 13/76
See application file for complete search history.

(56) References Cited

U.S. PATENT DOCUMENTS

| | | | | |
|---|---|---|---|---|
| 5,525,407 | A * | 6/1996 | Yang | A61F 13/15617 428/212 |
| H1575 | H * | 8/1996 | Daugherty | A61F 13/512 428/131 |
| H1575 | H * | 8/1996 | Daugherty | 428/131 |
| 5,795,344 | A * | 8/1998 | Chappell | A61F 13/533 604/379 |
| 2008/0015538 | A1* | 1/2008 | Deerin | A61F 13/505 604/402 |
| 2008/0208154 | A1* | 8/2008 | Oetjen | D04H 3/00 604/367 |
| 2012/0010584 | A1* | 1/2012 | Schmidt | A61F 13/00004 604/372 |
| 2012/0226250 | A1* | 9/2012 | Sato | A61F 13/51104 604/367 |
| 2013/0296739 | A1* | 11/2013 | Schultz | A61B 10/007 600/573 |

OTHER PUBLICATIONS http://www.merriam-webster.com/dictionary/surface.*
http://www.merriam-webster.com/dictionary/layer.*

* cited by examiner

*Primary Examiner* — Bradley H Philips

(57) ABSTRACT

A disposable undergarment that includes a waistband; an outside surface; an inner surface, where the inner surface includes absorbent non-woven material; a pocket within an inner crotch area, where the pocket includes an opening; and a pad, where the pad inserts into the pocket through the opening. The pad may include a top surface with a series of channels across the top surface. Further the pad according to the present invention may include varying degrees of density to encourage fluid flow away from the skin of the user.

1 Claim, 3 Drawing Sheets

DISPOSABLE MENSTRUAL UNDERGARMENT

BACKGROUND OF THE INVENTION

Field of Invention

The present invention relates to a disposable menstrual undergarment and system.

Description of Related Art

The use and development of undergarments specifically for use by women during their menstrual period is well known. The normal undergarment for a woman typically includes panties that are either cotton or other comparable cloth. Women use these typical undergarments on a daily basis. However, women undergarments may further include padding or insertable pads that absorb fluids during a woman's menstrual period. Further, other paddings have been developed to protect the vagina area during heavy perspiration or other fluid leakage that may occur. Other pads and systems have been developed to address a female's needs during menstrual period. These include sanitary napkins and pads that attach to traditional panty where the pads are typically removable and insertable by using an adhesive surface that's provided on one side of the pad. Further, tampons that insert within a woman's vagina have also been developed to assist a woman in absorbing menstrual fluids during menstruation. Some drawbacks to the use of pads and tampons is the leakage that may occur due to improper fit or insufficient padding that is provided by the pads or tampons. Leakage from the padding can be embarrassing and further, stain a woman's clothing especially in the crotch area of pants.

As a consequence, various disposable panties and other means of addressing feminine sanitary care have been developed. One technique that has been developed is the use of disposable undergarments or disposable panties, which provide additional protection for a woman during their menstrual cycle. The disposable undergarment may be worn directly against the woman's vaginal area and then any outer clothing may be worn on the outside of the undergarment. But even further improvements are necessary to provide a convenient and effective use of such an undergarment. Many of the disposable undergarments are bulky and do not provide sleek padding that's effective to absorb menstrual fluids and also provide comfortable wear for the woman.

SUMMARY OF THE INVENTION

The present invention relates to a disposable undergarment that includes a waistband; an outside surface; an inner surface, where the inner surface includes absorbent non-woven material; a pocket within an inner crotch area, where the pocket includes an opening; and a pad, where the pad inserts into the pocket through the opening. The pad may include a top surface with a series of channels across the top surface. Further the pad according to the present invention may include varying degrees of density to encourage fluid flow away from the skin of the user.

DETAILED DESCRIPTION

The present invention relates to a disposable menstrual undergarment that utilizes absorption in undergarment padding area to absorb fluids during use. The undergarment according to the present invention includes a pocket within the crotch area that receives various pads that are interchangeable by the user. Interchangeable padding enables a user to vary the type of padding that is used with the undergarment. The various under padding provides various degrees of absorption and comfort during use. Further, the undergarment according to the present invention has interior absorbent material throughout the inner surface of the undergarment that is sleek to provide a further or a secondary area of absorption that may be necessary during a heavy menstrual cycle.

Figure 1A:
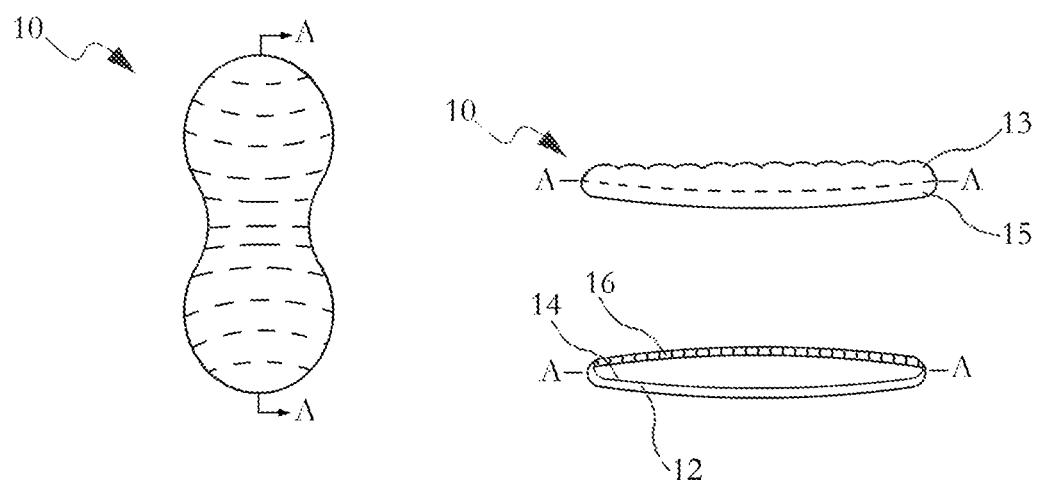
FIG. 1A depicts a first pad with two exemplary layering configurations for use in accordance with the present invention.

In reference to FIG. 1, a Pad 10 as depicted in accordance with the present invention. Pad 10 includes a top surface with a series of channels across the surface area. These channels help to direct the flow of fluids into the layers of the Pad 10. Further shown in FIG. 1A, the Pad 10 includes a system of layers that enables the storage of fluid and movement of fluid away from the skin surface of the user. Two embodiments of layer configurations are shown in FIG. 1A. In the first embodiment, at the cross section A-A, a first inside Layer 13 is depicted. The first inside layer 13 includes a ribbed surface and adjoins to an outside Layer 15. The inside Layer 13 has a first material density associated with it. The outside layer has a second material density. The Pad 10 of the present invention is preferably manufactured of non-woven fabric. The non-woven fabric may be created at various densities to create various absorption rates. The first density $D_1$ as illustrated with the inside Layer 13 is less than the second density $D_2$ of the outside Layer 15. This lesser density encourages the flow of fluids into the outside Layer 15. Therefore, the greater amount of fluids may be stored on this outside layer of Pad 10. This embodiment, therefore, helps to move the fluids away from the skin of the user. Further, an alternative embodiment is also shown in FIG. 1A where the Pad 10 cross section AA includes three layers of varying density. An inside Layer 16 is shown with a mid Layer 14 and an outside Layer 12. In this particular embodiment, the inside Layer 16 allows for the flow of fluids into the mid Layer 14 and the greatest density of materials provided in the outside Layer 12. This, again, moves the fluids away from the inside layer and away from the skin of the user. The fluids are primarily stored within the mid Layer 14 and the outside Layer 12 provides an additional layer of storage and protection to keep fluids within the mid Layer 14.

Figure 1B:
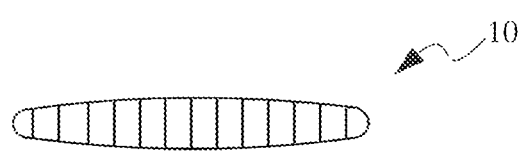
FIG. 1B depicts a side view of the first pad in accordance with the present invention.

FIG. 1B shows a side view of the Pad 10. Pad 10 includes channels that run along the side surface of the Pad 10 that encourages or urges the flow of fluids to the inner compartments of the Pad 10.

Figure 2:
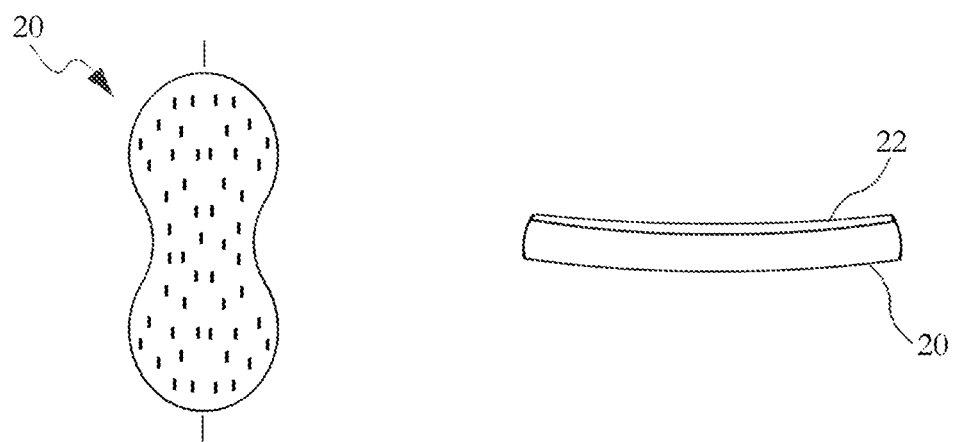
FIG. 2 depicts a second pad with a distinct layering configuration.
Figure 3:
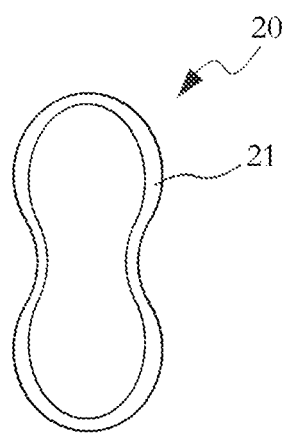
FIG. 3 depicts the second pad as alternative top surface.

FIG. 2 depicts a second embodiment of a Pad 20, used in accordance with the present invention. The Pad 20 includes a top surface that has a series of indentations over the top surface. The indentations encourage the flow of fluids into a top or an inside Layer 22, shown in FIG. 2. This inside Layer 22 abuts to a thicker outside Layer 20. In this particular embodiment, the inside layer has a thinner composition and a lesser density than the outside Layer 20. FIG. 3 depicts an alternative top surface use in accordance with the Pad 20 of FIG. 2. This top surface includes an inner pad Material 23 and an outer Border 21. Here, the flow of fluids is encouraged to the outer Border 21 that may have a higher density of material. Both the Pads 10 and 20 provides examples of pads used in conjunction with Panty 40 shown in FIG. 4.

Figure 4:
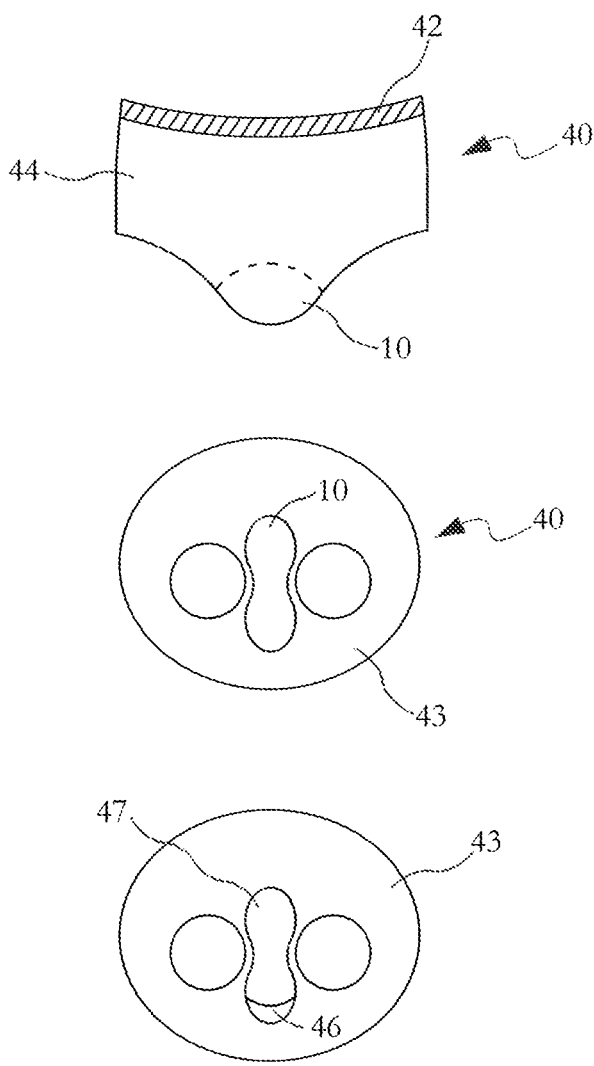
FIG. 4 depicts a panty with an insertion pocket that receives padding in accordance with the present invention.

The Panty 40 of FIG. 4 includes a Waistband 42 and an outside Surface 44. Shown in FIG. 4, is the insertion of Pad 10 into the crotch area of the Panty 40. An absorbent non-woven material is provided on the inner surface of 43 of Panty 40 that provides a sleek and efficient means to absorb any excess fluid that may leak from the Pad 10, once inserted into the Panty 40. A Pocket 47 is shown that receives padding into the pocket Opening 46.

During use, the absorbent and disposable Panty 40 is worn by a user that inserts a desired pad into the pocket Opening 46. As noted, the present invention uses various padding for insertion into the Opening 46. The advantage of the present invention is that the disposable garment provides a user with the flexibility of inserting the most effective pad into the pocket for a single use. If the disposable undergarment is suitable for continued use, the user may simply remove the padding, and insert a new pad within the disposable undergarment. Therefore, multiple pads may be used with a single disposable undergarment. However, since the undergarment may become soiled due to excessive leakage from the padding, the entire undergarment is disposable and a complete new undergarment is provided with new padding, as desired by the user. The present invention, therefore, provides flexibility of multiple padding for a disposable undergarment and maximum protection for the user during use.

In one alternative embodiment of the present invention, the Panty 40 may include the Pad 10 in one of the various styles or embodiments described above, however in this alternative embodiment the Pad 10 is permanently affixed within the Panty 40. The user of this alternative embodiment may therefore discard the entire Panty 40 after use thereof. As a consequence, Panty 40 in the alternative embodiment is disposable and the interchanging of the Pad 10 is unnecessary. So completely disposable Panty 40 may be provided with a variation of Pad 10 as shown above.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The exemplary embodiment was chosen and described in order to best explain the principles of the invention and its practical application, to thereby enable others skilled in the art to best utilize the invention and various embodiments with various modifications as are suited to the particular use contemplated.

What is claimed is:

1. A disposable undergarment comprising:
   a. a waistband;
   b. an outer surface;
   c. an inner surface that includes absorbent non-woven material, and said inner surface is adapted for contact with a user;
   d. a pocket within an inner crotch area of the inner surface, where the pocket includes an opening; and
   e. a pad, where the pad inserts into the pocket through the opening, and includes a top surface with a series of channels across the surface, where the pad includes an inside layer, a mid layer and an outside layer, the inside layer has a first density D1, the mid layer has a second density D2, and the outside layer has a third density D3, wherein $D1<D2<D3$, and the outside layer forms an outermost surface of the pad to encourage fluid flow away from the user.

\* \* \* \* \*